United States Patent
Weiss

(10) Patent No.: US 12,298,372 B2
(45) Date of Patent: May 13, 2025

(54) APPARATUS FOR OPTIMIZING A SEQUENCE OF MAGNETIC RESONANCE (MR) SCANS OF A MR EXAM

(71) Applicant: KONINKLIJKE PHILIPS N.V., Eindhoven (NL)

(72) Inventor: Steffen Weiss, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 173 days.

(21) Appl. No.: 18/028,788

(22) PCT Filed: Sep. 7, 2021

(86) PCT No.: PCT/EP2021/074592
§ 371 (c)(1),
(2) Date: Mar. 28, 2023

(87) PCT Pub. No.: WO2022/069166
PCT Pub. Date: Apr. 7, 2022

(65) Prior Publication Data
US 2023/0333187 A1    Oct. 19, 2023

(30) Foreign Application Priority Data
Sep. 29, 2020   (EP) .................................. 20198868

(51) Int. Cl.
G01R 33/54    (2006.01)
(52) U.S. Cl.
CPC ......... G01R 33/543 (2013.01); G01R 33/546 (2013.01)

(58) Field of Classification Search
CPC ..... A61B 5/055; A61B 5/7267; A61B 5/7275; A61B 5/0006; A61B 5/01; A61B 5/053;
(Continued)

(56) References Cited

U.S. PATENT DOCUMENTS 7,587,232 B2 * 9/2009 Sugiura .................. A61B 5/055
324/307
8,600,476 B2 * 12/2013 Bi .......................... A61B 5/055
600/410

(Continued)

FOREIGN PATENT DOCUMENTS

EP    3381353 A1   10/2018
WO   2012049634 A1   4/2012
(Continued)

OTHER PUBLICATIONS

International Search Report and Written Opinion from PCT/EP2021/074592 mailed Dec. 7, 2021.
(Continued)

*Primary Examiner* — Vinh P Nguyen

(57) ABSTRACT

An apparatus for optimizing a sequence of Magnetic Resonance (MR) scans of an MR exam. The apparatus includes an input unit; a processing unit; and an output unit. The input unit is configured to receive information on a MR exam to be performed on a patient, the information includes details of individual MR scans; provide the information to the processing unit; receive information on the patient, and provide the information to the processing unit. The processing unit is configured to utilize the information to determine an overall score value for each MR scan of the individual MR scans and determine a sequence of MR scans for the MR exam comprising utilization of the individual MR scans and
(Continued)

the overall score value for each MR scan. The output unit is configured to output the determined sequence of MR scans for the MR exam.

15 Claims, 2 Drawing Sheets

(58) Field of Classification Search
CPC ......... A61B 8/00; A61B 5/0205; A61B 6/507; A61B 5/4023; A61B 5/4076; A61B 5/4082; A61B 5/103; A61B 5/24; A61B 2562/0238; A61B 2576/00; A61B 3/107; A61B 5/0515; A61B 5/4094; A61B 5/002; G01R 33/543; G01R 33/546; G01R 33/56509; G01R 33/58; G01R 33/0385; G01R 33/32; G01R 33/12; G01R 33/56366; G01R 33/565; G01R 33/48; G01R 33/445; G01R 33/0023; G01R 33/481; G01R 33/4808; G16H 40/63; G06T 2207/10088; G06T 7/0014; G06T 2207/10081; G06T 2207/10116; G06T 2207/30168; G06T 7/0012; G01N 27/72; G01N 24/08
See application file for complete search history.

(56) References Cited

U.S. PATENT DOCUMENTS

| | | | | |
|---|---|---|---|---|
| 8,958,866 | B2* | 2/2015 | Bolar | G01R 33/5607 |
| | | | | 324/309 |
| 10,067,211 | B2* | 9/2018 | Dagher | G01R 33/4806 |
| 11,257,585 | B2* | 2/2022 | Bhatia | G06T 7/0012 |
| 11,574,728 | B2* | 2/2023 | Amthor | G01R 33/543 |
| 2015/0123657 | A1 | 5/2015 | Rapoport | |
| 2020/0008703 | A1 | 1/2020 | Zeller | |
| 2020/0104674 | A1 | 4/2020 | Vellagoundar et al. | |
| 2022/0386949 | A1* | 12/2022 | Weiss | A61B 5/055 |

FOREIGN PATENT DOCUMENTS

| | | |
|---|---|---|
| WO | 2013165571 A1 | 11/2013 |
| WO | 2018178148 A1 | 10/2018 |

OTHER PUBLICATIONS https://en.wikipedia.org/wiki/List_of_cognitive_biases (downloaded Feb. 28, 2023).
https://en.wikipedia.org/wiki/Peak%E2%80%93end_rule (downloaded Feb. 28, 2023).

* cited by examiner

APPARATUS FOR OPTIMIZING A SEQUENCE OF MAGNETIC RESONANCE (MR) SCANS OF A MR EXAM

CROSS REFERENCE TO RELATED APPLICATIONS

This application is a U.S. national phase application of International Application No. PCT/EP2021/074592 filed on Sep. 7, 2021, which claims the benefit of EP Application Serial No. 20198868.0 filed on Sep. 29, 2020 and is incorporated herein by reference.

FIELD OF THE INVENTION

The present invention relates to an apparatus for optimising a sequence of Magnetic Resonance (MR) scans of a MR exam, an imaging system, a method for optimising a sequence of Magnetic Resonance (MR) scans of a MR exam, as well as to a computer program element and a computer readable medium.

BACKGROUND OF THE INVENTION

MR exams, carried out by a Magnetic Resonance Imaging (MRI) scanner or system, typically consist of at least a handful of different scans providing different image contrasts (anatomic scout scans, T1-weighted, T2-weighted, T2*-weighted) and providing different functional information (perfusion, diffusion, vascular flow, tissue viability). These scans of the MR exam have very different properties in terms of duration, sensitivity to motion, and MR noise level.

For most types of MR scans a trade-off can be chosen between duration and image quality because longer scans offer more image quality. A similar trade-off exists between scan duration and MR noise level, because shorter scans are generally louder.

However, there is a need to provide a mechanism to optimise MR exams.

US 2015/123657 A1 describes a method of operating a magnetic resonance imaging (MRI) device for habituating a patient and/or user to acoustic-noise of the device's operation.

WO 2013/165571 A1 describes a system and method for performing quiet magnetic resonance imaging.

EP 3 381 353 A1 describes a method for planning an imaging scan protocol to be performed by a scanning imaging system.

US 2020/008703 A1 describes a method for monitoring a patient during a medical imaging examination.

SUMMARY OF THE INVENTION

It would be advantageous to have improved means of optimising MR exams. The object of the present invention is solved with the subject matter of the independent claims, wherein further embodiments are incorporated in the dependent claims. It should be noted that the following described aspects and examples of the invention apply also to the apparatus for optimising a sequence of Magnetic Resonance (MR) scans of a MR exam, the imaging system, the method for optimising a sequence of Magnetic Resonance (MR) scans of a MR exam, as well as to a computer program element and a computer readable medium.

In a first aspect, there is provided an apparatus for optimising a sequence of Magnetic Resonance (MR) scans of a MR exam. The apparatus comprises:
  an input unit;
  a processing unit; and
  an output unit.

The input unit is configured to receive information on a MR exam to be performed on a patient, the information comprising details of individual MR scans of the MR exam, and the input unit is configured to provide the information on the MR exam to the processing unit. The input unit is configured to receive information on the patient on whom the MR exam is to be performed. The information relates to the tolerance to noise of the patient and/or the ability of the patient to remain quiescent. The input unit is configured to provide the information on the MR patient to the processing unit. The processing unit is configured to utilize the information on the patient to determine an overall score value for each MR scan of the individual MR scans. The processing unit is configured to determine a sequence of MR scans for the MR exam comprising utilization of the individual MR scans and the overall score value for each MR scan. The output unit is configured to output the determined sequence of MR scans for the MR exam.

In this way, the scan sequence of a MR exam can be tailored for the type of person, or indeed the specific person, who is to undertake the MR scan. This means that the MR exam can be sequenced in such a way, that the different individual scans of the MR exam, that are generally of different durations and noise levels, can be ordered in order to maximise the effectiveness of the MR exam, in terms of quality of imagery acquired. Also, the comfort and experience provided to the patient can be ensured.

In an example, the details on the individual MR scans comprises information on a noise level of each MR scan. The processing unit is configured to determine a noise score value for each MR scan of the individual MR scans, and wherein the overall score value for each MR scan comprises the noise score value for each MR scan.

In an example, the information on the tolerance to noise for the patient comprises one or more of: an age of the patient; information on previous MR exams the patient has undertaken including whether the patient has previously undertaken an MR exam; questionnaire information provided by the patient.

Thus, in being provided with information regarding how a patient tolerates or withstands noise, where an MR scan sequence can generate significant noise, enables the scan sequence to be ordered such that the discomfort to the patient is minimised, the chances of the patient moving during an individual scan is decreased, and the patient's overall experience of how pleasant the scan was will be maximised. Thus, in addition to obtaining as good a quality MR exam as possible, reducing the need to repeat the MR exam or certain scans, the patient's overall view of the MR exam will be as positive as possible, ensuring that the compliance of the patient will be as high as possible for any follow-on or future MR exam the patient will have.

In an example, the details on the individual MR scans comprises information on a duration of each MR scan. The processing unit is configured to determine a duration score value for each MR scan of the individual MR scans. The overall score value for each MR scan comprises the duration score value for each MR scan.

In this manner, by being provided with information regarding how a patient tolerates or withstands lying still for periods of time in the core of the MRI scanner in a confined space with very loud noises being generated in what can be a very intimidating experience, enables the scan sequence to be ordered such that the discomfort to the patient is minimised, the chances of the patient moving during an individual scan is decreased, and the patient's overall experience of how pleasant the scan was will be maximised. Thus, in addition to obtaining as good a quality MR exam as possible, reducing the need to repeat the MR exam or certain scans, the patient's overall view of the MR exam will be as positive as possible, ensuring that the compliance of the patient will be as high as possible for any follow-on or future MR exam the patient will have.

In an example, the information on the ability of the patient to remain quiescent for different periods of time comprises one or more of: an age of the patient; information on previous MR exams the patient has undertaken including whether the patient has previously undertaken an MR exam; questionnaire information provided by the patient.

In an example, the processing unit is configured to place an MR scan in the second half of the sequence of MR scans and optionally as the last scan of the sequence of MR scans based on the MR scan of the individual MR scans that has the lowest overall score.

In other words, a scoring system can be utilized that scores most unpleasant scans with a high score value, and most pleasant scans with a low score value. Clearly, this scoring could be vice-versa, and the last scan could then be the one with the highest overall score.

It has been found that a human's perception of an overall experience is affected to a disproportionately large degree by what happens during the end period or right at the end of the overall experience. Thus, if a particularly unpleasant part of the overall experience was at the end of the overall experience, the patient will view the overall experience more negatively than if that unpleasant part of the experience was earlier in the sequence. Also, this feeling of what is unpleasant is different for different people, where some people find a very loud noise for a short or medium length period not to be unpleasant, but do not like to have back-to-back scans where each requires no movement, whilst another patient may have no problem lying still for long periods, but a scans of high noise cause anxiety if of too long a duration of if a sequence of back-to-back scans were to all be very loud. Thus, by taking this information into account, a tailored scan sequence can be generated that mitigates these issues in different ways for different people.

In an example, the scan in the second half of the sequence of MR scans and optionally the last scan is the MR scan of the individual MR scans that has the lowest overall score.

In other words, the actual scan of the individual scans presented to the input unit, that has the lowest overall score, is used as the near to last or last scan.

In an example, the scan in the second half of the sequence of MR scans and optionally the last scan is a modified MR scan of the individual MR scan that has the lowest overall score. The processing unit is configured to modify the MR scan based on its overall score.

In other words, the actual scan of the individual scans presented to the input unit, that has the lowest overall score, can be identified as the most appropriate scan to be used as the near to last or last scan. However, it can be determined that by reducing, for example the duration and/or scan parameters in order to reduce the noise of this last (or near last) scan, the perception of the overall scan for this particular person could be significantly improved with respect to using an unmodified scan.

In an example, the modification of the MR scan comprises one or more of: a reduction in duration of the MR scan; a change in at least one parameter of the MR scan to effect a reduction in noise level of the MR scan.

In an example, the processing unit is configured to place at least one MR scan at positions within the sequence of MR scans based on the at least one MR scan of the individual MR scans that has the at least one highest overall score.

In an example, the at least MR scan at positions within the sequence of MR scans is the at least one MR scan of the individual MR scans that has the at least one highest overall score.

In an example, the at least MR scan at positions within the sequence of MR scans is a modified at least one MR scan of the individual MR scans that has the at least one highest overall score. The processing unit is configured to modify the at least one MR scan based on the overall score of the at least one scan.

Thus, the most unpleasant scan can be located appropriately within the scan sequence to reduce the overall effect of that scan, and if there are a number of equally, or nearly equal scan of equal unpleasantness, then these can for example be uniformly spread throughout the scan sequence, except towards the end, in order to maximise the patient's overall perception of the MR exam, and to maximise the effectiveness of the MR exam in terms of individual scan quality.

In an example, the modification of the MR scan comprises one or more of: a reduction in duration of the at least one MR scan; a change in at least one parameter of the at least one MR scan to effect a reduction in noise level of the at least one MR scan.

In a second aspect, there is provided an imaging system, comprising:
 a Magnetic Resonance Imaging "MRI" unit; and
 an apparatus according to the first aspect;
The MRI unit is configured to carry out the sequence of MR scans for the MR exam for the patient determined by the apparatus.

In a third aspect, there is provided a method for optimising a sequence of Magnetic Resonance (MR) scans of a MR exam, the method comprising:
 a) receiving by an input unit information on a MR exam to be performed on a patient, the information comprising details of individual MR scans of the MR exam;
 b) providing by the input unit the information on the MR exam to a processing unit;
 c) receiving by the input unit information on the patient on whom the MR exam is to be performed, wherein the information relates to the tolerance to noise of the patient and/or the ability of the patient to remain quiescent;
 d) providing by the input unit the information on the MR patient to the processing unit;
 e) determining by the processing unit an overall score value for each MR scan of the individual MR scans, the determining comprising utilizing the information on the patient;
 f) determining by the processing unit a sequence of MR scans for the MR exam, the determining comprising utilizing the individual MR scans and the overall score value for each MR scan; and
 g) outputting by the output unit the determined sequence of MR scans for the MR exam.

According to another aspect, there is provided a computer program element controlling one or more of the apparatuses or system as previously described which, if the computer program element is executed by a processing unit, is adapted to perform one or more of the methods as previously described.

According to another aspect, there is provided a computer readable medium having stored computer element as previously described.

The computer program element can for example be a software program but can also be a FPGA, a PLD or any other appropriate digital means.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawing.

DETAILED DESCRIPTION OF EMBODIMENTS

Figure 1:
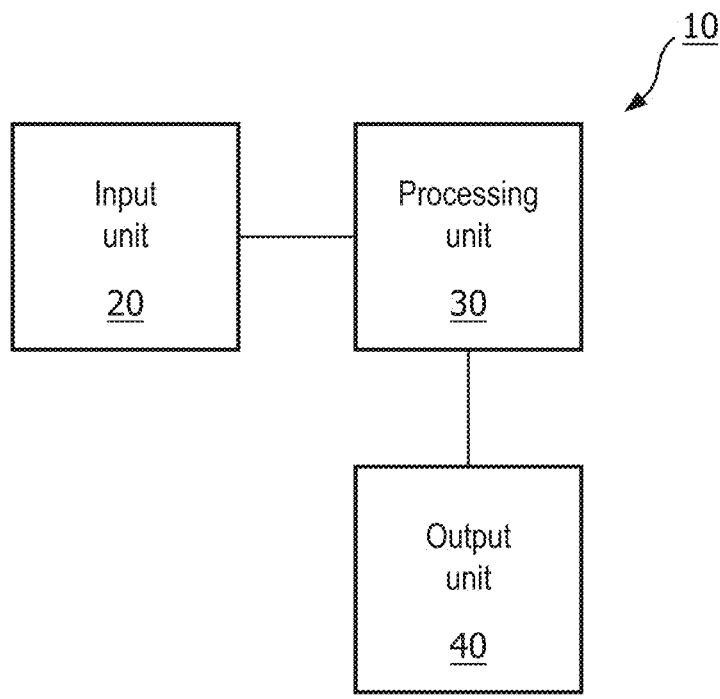
FIG. 1 shows a schematic set up of an example of an apparatus for optimising a sequence of Magnetic Resonance (MR) scans of a MR exam.

FIG. 1 shows a schematic example of an apparatus 10 for optimising a sequence of Magnetic Resonance (MR) scans of a MR exam. The apparatus comprises an input unit 20, a processing unit 30, and an output unit 40. The input unit is configured to receive information on a MR exam to be performed on a patient. The information comprises details of individual MR scans of the MR exam. The input unit is configured to provide the information on the MR exam to the processing unit. The input unit is configured to receive information on the patient on whom the MR exam is to be performed. The input unit is configured to provide the information on the MR patient to the processing unit. The processing unit is configured to utilize the information on the patient to determine an overall score value for each MR scan of the individual MR scans. The processing unit is configured to determine a sequence of MR scans for the MR exam comprising utilization of the individual MR scans and the overall score value for each MR scan. The output unit is configured to output the determined sequence of MR scans for the MR exam.

According to an example, the details on the individual MR scans comprises information on a noise level of each MR scan. The information on the patient comprises information on a tolerance to noise for the patient. The processing unit is configured to utilize the information on a tolerance to noise for the patient to determine a noise score value for each MR scan of the individual MR scans. The overall score value for each MR scan comprises the noise score value for each MR scan.

According to an example, the information on the tolerance to noise for the patient comprises one or more of: an age of the patient; information on previous MR exams the patient has undertaken including whether the patient has previously undertaken an MR exam; questionnaire information provided by the patient.

According to an example, the details on the individual MR scans comprises information on a duration of each MR scan. The information on the patient comprises information on an ability of the patient to remain quiescent for different periods of time. The processing unit is configured to utilize the information on an ability of the patient to remain quiescent for different periods of time to determine a duration score value for each MR scan of the individual MR scans. The overall score value for each MR scan comprises the duration score value for each MR scan.

According to an example, the information on the ability of the patient to remain quiescent for different periods of time comprises one or more of: an age of the patient; information on previous MR exams the patient has undertaken including whether the patient has previously undertaken an MR exam; questionnaire information provided by the patient.

According to an example, the processing unit is configured to place an MR scan in the second half of the sequence of MR scans and optionally as the last scan of the sequence of MR scans based on the MR scan of the individual MR scans that has the lowest overall score.

According to an example, the scan in the second half of the sequence of MR scan and optionally the last scan is the MR scan of the individual MR scans that has the lowest overall score.

According to an example, the scan in the second half of the sequence of MR scans and optionally the last scan is a modified MR scan of the individual MR scans that has the lowest overall score, and wherein the processing unit is configured to modify the MR scan based on its overall score.

According to an example, the modification of the MR scan comprises one or more of: a reduction in duration of the MR scan; a change in at least one parameter of the MR scan to effect a reduction in noise level of the MR scan.

According to an example, the processing unit is configured to place at least one MR scan at positions within the sequence of MR scans based on the at least one MR scan of the individual MR scans that has the at least one highest overall score.

According to an example, the at least MR scan at positions within the sequence of MR scans is the at least one MR scan of the individual MR scans that has the at least one highest overall score.

According to an example, the at least MR scan at positions within the sequence of MR scans is a modified at least one MR scan of the individual MR scans that has the at least one highest overall score. The processing unit is configured to modify the at least one MR scan based on the overall score of the at least one scan.

According to an example, the modification of the MR scan comprises one or more of: a reduction in duration of the at least one MR scan; a change in at least one parameter of the at least one MR scan to effect a reduction in noise level of the at least one MR scan.

Figure 2:
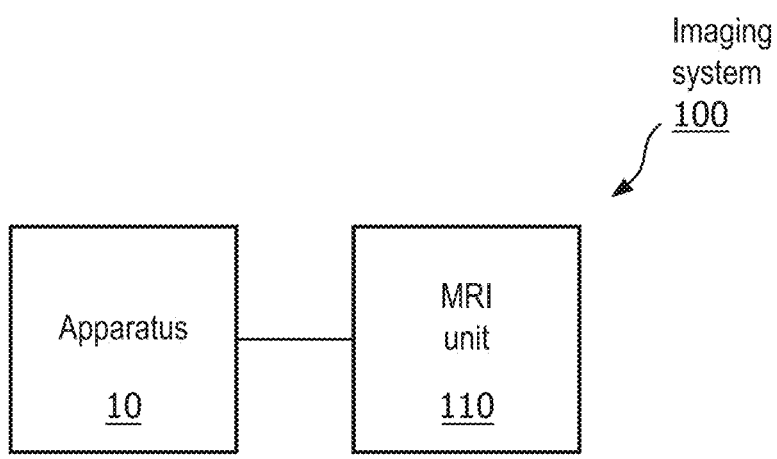
FIG. 2 shows a schematic set up of an example of an imaging system.

FIG. 2 shows a schematic example of an imaging system 100. The imaging system comprises a Magnetic Resonance Imaging "MRI" unit 110 and an apparatus 10 as described above with respect to FIG. 1. The MRI unit is configured to carry out the sequence of MR scans for the MR exam for the patient determined by the apparatus.

Figure 3:
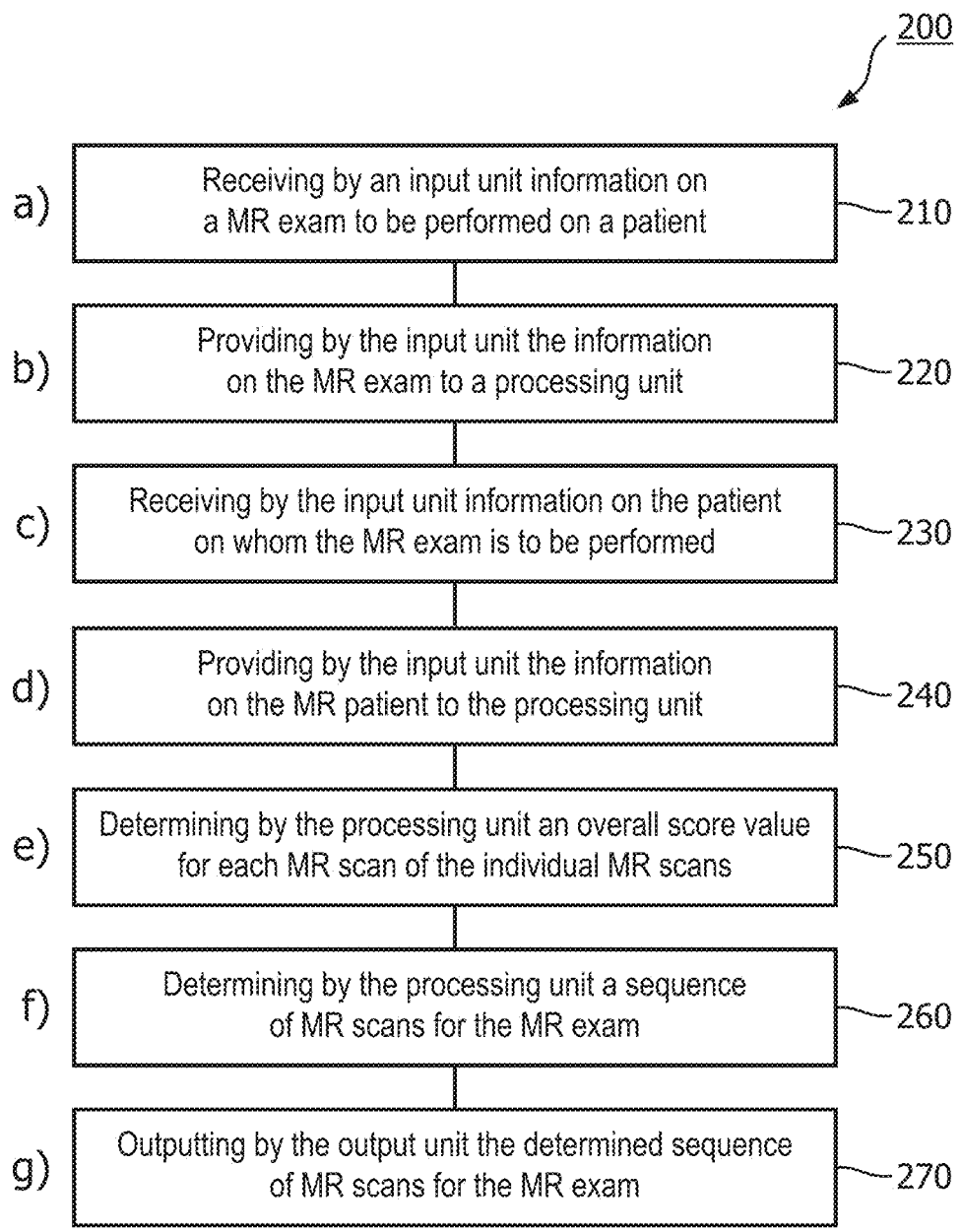
FIG. 3 shows a method for optimising a sequence of Magnetic Resonance (MR) scans of a MR exam.

FIG. 3 shows a method 200 for optimising a sequence of Magnetic Resonance (MR) scans of a MR exam in its basic steps. The method comprises:

in a receiving step 210, also referred to as step a), receiving by an input unit information on a MR exam to be performed on a patient, the information comprising details of individual MR scans of the MR exam;

in a providing step 220, also referred to as step b), providing by the input unit the information on the MR exam to a processing unit;

in a receiving step 230, also referred to as step c), receiving by the input unit information on the patient on whom the MR exam is to be performed;

in a providing step 240, also referred to as step d), providing by the input unit the information on the MR patient to the processing unit;

in a determining step 250, also referred to as step e), determining by the processing unit an overall score value for each MR scan of the individual MR scans, the determining comprising utilizing the information on the patient;

in a determining step 260, also referred to as step f), determining by the processing unit a sequence of MR scans for the MR exam, the determining comprising utilizing the individual MR scans and the overall score value for each MR scan; and in an outputting step 270, also referred to as step g), outputting by the output unit the determined sequence of MR scans for the MR exam.

In an example, the details on the individual MR scans comprises information on a noise level of each MR scan. The information on the patient comprises information on a tolerance to noise for the patient. Step e) then comprises determining a noise score value for each MR scan of the individual MR scans, and the overall score value for each MR scan comprises the noise score value for each MR scan.

In an example, the information on the tolerance to noise for the patient comprises one or more of: an age of the patient; information on previous MR exams the patient has undertaken including whether the patient has previously undertaken an MR exam; questionnaire information provided by the patient.

In an example, the details on the individual MR scans comprises information on a duration of each MR scan. The information on the patient comprises information on an ability of the patient to remain quiescent for different periods of time. Step e) then comprises determining a duration score value for each MR scan of the individual MR scans, and the overall score value for each MR scan comprises the duration score value for each MR scan.

In an example, the information on the ability of the patient to remain quiescent for different periods of time comprises one or more of: an age of the patient; information on previous MR exams the patient has undertaken including whether the patient has previously undertaken an MR exam; questionnaire information provided by the patient.

In an example, wherein step f) comprises placing by the processing unit an MR scan in the second half of the sequence of MR scans and optionally as the last scan of the sequence of MR scans based on the MR scan of the individual MR scans that has the lowest overall score In an example, the scan in the second half of the sequence of MR scan and optionally the last scan is the MR scan of the individual MR scans that has the lowest overall score.

In an example, the scan in the second half of the sequence of MR scans and optionally the last scan is a modified MR scan of the individual MR scans that has the lowest overall score. Step f) then comprises modifying by the processing unit the MR scan based on its overall score.

In an example, the modification of the MR scan comprises one or more of: reducing a duration of the MR scan; changing at least one parameter of the MR scan to effect a reduction in noise level of the MR scan.

In an example, step f) comprises placing by the processing unit at least one MR scan at positions within the sequence of MR scans based on the at least one MR scan of the individual MR scans that has the at least one highest overall score.

In an example, the at least MR scan at positions within the sequence of MR scans is the at least one MR scan of the individual MR scans that has the at least one highest overall score.

In an example, the at least MR scan at positions within the sequence of MR scans is a modified at least one MR scan of the individual MR scans that has the at least one highest overall score, and step f) comprises modifying by the processing unit the at least one MR scan based on the overall score of the at least one scan.

In an example, the modifying the at least one MR scan comprises one or more of: changing at least one duration of the at least one MR scan; changing at least one parameter of the at least one at least one noise level of the at least one MR scan.

Thus, a new technique of automatically optimising a sequence of Magnetic Resonance (MR) scans of a MR exam is based on the insight that when humans memorize an experience consisting of a sequence of events the individual events do not equally contribute to the overall perception of the experience. Perception is rather dominated by the most extreme event and the last event in that sequence. For example, if you give some additional very moderate pain to a human at the end of a sequence of pain events, the subject will rate this sequence with additional (very moderate) pain at the end as more pleasant than the sequence without the additional (very moderate) pain at the end, but which ended with a higher pain level. This holds as long as the additional last pain event is much less severe than most of the others in that sequence. Indeed, various types of human perception bias are known, in a sense that humans sense stimuli or perceive events not objectively like a measurement system but rather biased in some form. The above described peak-end perception bias is one example of this. It was realised that not only could the MR scans of a sequence making up a MR exam be placed in a sequence order that maximises the patient's perception of how "pleasant" the experience was (or minimise how unpleasant it was) and therefore make them better subjects for follow-on MR exams, but an optimised sequence scan would also provide for better image quality. This is because the patient would be less likely to move or indeed panic and press an alarm-stop button, both of which would have required a repeat of one or more of the scans if not of the entire MR exam.

The new technique provides the following. For most types of MR scans a trade-off can be chosen between duration and image quality because longer scans offer more image quality. A similar trade-off exists between scan duration and MR noise level, because shorter scans are generally louder. The new technique provides the ability to find the optimum in these trade-offs. Duration and MR noise level are on the other hand quantities that directly affect patient experience. Patient experience will be generally improved for shorter and less loud scans. The new technique then enables a balance to be found between clinically desirable quantities as high image quality and scan speed and patient comfort and experience on the other hand, taking into account personal preferences that may differ from patient to patient as far as MR noise and scan duration are concerned. The new technique enables an automatic arrangement of the scan sequence to be generated, where scans with contrast agent can be outside of this arrangement because they are generally acquired at a specific point in a scan sequence.

The apparatus for optimising a sequence of Magnetic Resonance (MR) scans of a MR exam, the imaging system, and the method for optimising a sequence of Magnetic Resonance (MR) scans of a MR exam are now described in further detail with respect to specific embodiments.

As discussed above, the apparatus is based on a first insight that in many exams the absence of clinical and technical constraints on the order of scans offers the possibility to perform this choice such that patient experience is optimized. The new technique is secondly based on the insight that relevant patient experience is related to the remembrance of the MR exam, rather than the current or actual patient experience as it occurs to the patient during the exam. Relevant here means that patients with a more positive experience in remembrance will:

- be more compliant and capable in immediate post-imaging workflow, which speeds this up and requires less aftercare by staff, e.g. during leaving the imaging suite, dressing up again, understanding information on next steps;
- recover better and faster from the stress of the imaging exam which allows subject patients to progress earlier to next steps in the hospital workflow than would otherwise be possible;
- speed up and improve image quality of any follow-up scans, because patients with a more positive experience/reduced anxiety are more co-operative
- provide a better net promoter score, which is an important metric for clinical departments The new technique is thirdly based on the insight that the remembrance of an MR exam is subject to the human peak-end perception bias. Specifically, the most extreme perceptions in any of these scans and the pleasantness of the last scan largely determine the relevant patient experience.

In summary the new technique involves the following:

- rank all scans with respect to pleasantness according to generally known preferences or even personal preferences of the patient;
- arrange the most pleasant scan at the end of the exam. This uses the peak-end-bias to improve patient experience without any impact on exam duration or image quality;
- determine the most unpleasant scan and increase its pleasantness along the trade-offs involving duration and MR noise level as described above. This uses the peak-end-bias to largely improve patient experience with minimal impact on overall scan efficiency, because only the selected scan is slowed down.

The following provides specific details on certain aspects of the new technique.

Obtaining Preferences in Terms of Pleasantness Per Patient Group

Preferences of patients differ by patient group. Younger patients for example prefer a short and rather louder scan than a longer and quiet scan, because especially children are not as much disturbed by loud noise as the elderly are. However, children can find it particularly disturbing to endure a long scan or exam in which they have to keep still, while this is not be a major problem for many adults.

Thus, the new technique involves defining heuristic, a priori, preferences per type of scan parameterized by scan duration, scan noise, and motion sensitivity and per patient group (or indeed individuals with that group) along these and further rules.

Also, the new technique involves obtaining statistical data of tolerance/pleasantness per type of scan parameterized by scan duration, scan noise, and motion sensitivity. These can be obtained by evaluating the percentage of scans that had to be interrupted per scan and per patient group. It can also be based on an in-exam questionnaire with questions like: "How would you rate the pleasantness of the last scan on a scale from 1 to 5?" It can also be based on a questionnaire after the exam.

Obtaining Personal Preferences of the Patient

Personal preferences can also be obtained by any kind of collection of information from the patient, e.g., by a questionnaire before the exam with questions like: "Would you rather prefer a louder and shorter scan or a quieter and longer scan?" "Would you prefer to keep very still for a short while or be allowed to move slightly but then have a longer scan?" "Would you prefer a short scan and hold your breath a couple of times for this, or would you like to breathe normally and accept a longer scan for this?"

The information of preference can be collected in a number of different ways in addition to questionnaire information.

First time patients can be presented with an augmented reality simulation headset and asked to lie down on a table to simulate the scan noise, bore movement, scan instructions, breath holding so as to elicit responses to personal preferences.

Personal preferences can also be derived from known personal patient characteristics such as past experiences and current patient condition. Patients with impaired hearing may not find loud scans as unpleasant as patients with un-impaired hearing, if it is safe to subject them to loud noise. Patients with attention deficit hyperactivity disorder (ADHD) can find it particularly unpleasant to be forced to keep still for longer times. Patients with respiratory disorders can find breath hold scans very unpleasant. Patients with claustrophobia can find those scans where their head is inside the inside bore particularly unpleasant.

Ranking of Scans with Respect to Pleasantness

Each scan is analysed for parameters that affect pleasantness, at least scan noise, scan duration, and motion sensitivity. This can be done by simple analysis of the scan type and scan parameters as known to MR experts. These three parameters are then transferred into pleasantness by an empirical function that may be based on rules with weighting parameters, or look-up tables. As commonly done in such functions, it can consist of several terms each with a weighting factor to adjust the relative strength of the term. The function may include parameters that depend on extractions from the statistical data mentioned above. The function may contain parameters that depend on personal data as answers to the questionnaire or patient condition as mentioned above. As a result, an overall pleasantness index (or score) is calculated for each scan of the exam.

Determination of Most and Least Pleasant Scan

Firstly, the most pleasant scan is determined. Secondly, the least pleasant scan/or scans is/are identified. Thus to account for several similarly unpleasant scans, the least pleasant 20% of scans (or a smaller or larger percentage) can be identified, where 100% corresponds to the duration of all scans.

Modification of Most Pleasant Scan

The most pleasant scan can however still be improved in pleasantness using the trade-offs mentioned above to provide for a more optimised scan, but this is not essential to do. Thus, this is done to selectively improve pleasantness for this scan as measured by the function mentioned above.

Trade-offs include e.g. converting scan duration into noise and vice versa. The range of how far along these trade-offs scans can be changed is determined by the MR apparatus processing unit and the software it runs, using for example the scoring system as described.

Modification of Least Pleasant Scan(s)

The least pleasant scan(s) is/are then also modified using the same trade-offs. This is done to selectively improve pleasantness for these scans as measured by the function mentioned above. Note, that this selective modification of most pleasant and least pleasant scan(s) leaves all other scans as optimized for image quality and short scan duration and thus will change overall quality and efficiency of the entire exam only marginally.

Determination of Scan Order

At last stage, the most pleasant scan is put last in scan order. The least pleasant scans are distributed within the exam well before its end, with breaks with more pleasant scans in-between, if there are several particular unpleasant scans. The patient may be automatically informed that there will be a (single) next scan which is somewhat unpleasant, because this may ease the situation for him/her.

As a result, patients will be more compliant and co-operative in immediate post-imaging workflow and in follow up procedures, which will improve speed and image quality of these scans. If a child is e.g. more positive about a first exam, it will more likely co-operate in the next. Vice versa, if it is initially severely disturbed, it may not co-operate, lower image quality, add time, or even require sedation in later exams.

Embodiment for Optimization of Entire Workflow from Home to Hospital and Home Again It is generally not possible to change the order of events of the entire workflow in a sense that the most pleasant event one is put last. Therefore, in certain situations a particularly pleasant event is added at the end of the entire workflow, e.g. in form of a guiding app issuing an overview of all was what achieved and a compliment to the patient for good compliance.

Such pleasant events can be added separately at the end of each phase of events, e.g. at the end of patient information and training at home.

A questionnaire completion task can be performed to rate all events of the home to home workflow in terms of pleasantness, in particular to identify the most unpleasant event. This provides the chance to improve on this event.

In another exemplary embodiment, a computer program or computer program element is provided that is characterized by being configured to execute the method steps of the method according to one of the preceding embodiments, on an appropriate apparatus or system.

The computer program element might therefore be stored on a computer unit, which might also be part of an embodiment. This computing unit may be configured to perform or induce performing of the steps of the method described above. Moreover, it may be configured to operate the components of the above described apparatus and/or system. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, USB stick or the like, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for optimizing a sequence of magnetic resonance (MR) scans of a MR exam, the apparatus comprising:
an input unit;
a processing unit; and
an output unit;
wherein, the input unit is configured to receive information on a MR exam to be performed on a patient, the information comprising details of individual MR scans of the MR exam, and wherein the input unit is configured to provide the information on the MR exam to the processing unit;

wherein, the input unit is configured to receive information on the patient on whom the MR exam is to be performed, wherein the information relates to the tolerance to noise of the patient and/or the ability of the patient to remain quiescent, and wherein the input unit is configured to provide the information on the MR patient to the processing unit;

wherein, the processing unit is configured to utilize the information on the patient to determine an overall score value for each MR scan of the individual MR scans;

wherein, the processing unit is configured to determine a sequence of MR scans for the MR exam comprising utilization of the individual MR scans and the overall score value for each MR scan; and wherein, the output unit is configured to output the determined sequence of MR scans for the MR exam.

2. The apparatus according to claim 1, wherein the details on the individual MR scans comprises information on a noise level of each MR scan, and information relating to the tolerance to noise of the patient wherein the processing unit is configured to determine a noise score value for each MR scan of the individual MR scans, and wherein the overall score value for each MR scan comprises the noise score value for each MR scan.

3. The apparatus according to claim 2, wherein the information on the tolerance to noise for the patient comprises one or more of: an age of the patient; information on previous MR exams the patient has undertaken including whether the patient has previously undertaken an MR exam; questionnaire information provided by the patient.

4. The apparatus according to claim 1, wherein the details on the individual MR scans comprises information on a duration of each MR scan, and information relating to the ability of the patient to remain quiescent, wherein the processing unit is configured to determine a duration score value for each MR scan of the individual MR scans, and wherein the overall score value for each MR scan comprises the duration score value for each MR scan.

5. The apparatus according to claim 4, wherein the information on the ability of the patient to remain quiescent for different periods of time comprises one or more of: an age of the patient; information on previous MR exams the patient has undertaken including whether the patient has previously undertaken an MR exam; questionnaire information provided by the patient.

6. The apparatus according to claim 1, wherein the processing unit is configured to place an MR scan in the second half of the sequence of MR scans and optionally as the last scan of the sequence of MR scans based on the MR scan of the individual MR scans that has the lowest overall score.

7. The apparatus according to claim 6, wherein the scan in the second half of the sequence of MR scan and optionally the last scan is the MR scan of the individual MR scans that has the lowest overall score.

8. The apparatus according to claim 6, wherein the scan in the second half of the sequence of MR scans and optionally the last scan is a modified MR scan of the individual MR scans that has the lowest overall score, and wherein the processing unit is configured to modify the MR scan based on its overall score; and optionally wherein the modification of the MR scan comprises one or more of: a reduction in duration of the MR scan; a change in at least one parameter of the MR scan to effect a reduction in noise level of the MR scan.

9. Apparatus The apparatus according to claim 1, wherein the processing unit is configured to place at least one MR scan at positions within the sequence of MR scans based on the at least one MR scan of the individual MR scans that has the at least one highest overall score.

10. The apparatus according to claim 9, wherein the at least MR scan at positions within the sequence of MR scans is the at least one MR scan of the individual MR scans that has the at least one highest overall score.

11. The apparatus according to claim 9, wherein the at least MR scan at positions within the sequence of MR scans is a modified at least one MR scan of the individual MR scans that has the at least one highest overall score, and wherein the processing unit is configured to modify the at least one MR scan based on the overall score of the at least one scan.

12. The apparatus according to claim 11, wherein the modification of the MR scan comprises one or more of: a reduction in duration of the at least one MR scan; or a change in at least one parameter of the at least one MR scan to effect a reduction in noise level of the at least one MR scan.

13. An imaging system, comprising:
a magnetic resonance imaging (MRI) unit; and
an apparatus according to claim 1;
wherein, the MRI unit is configured to carry out the sequence of MR scans for the MR exam for the patient determined by the apparatus.

14. A method for optimising a sequence of magnetic resonance scans of a MR exam, the method comprising:
a) receiving by an input unit information on a MR exam to be performed on a patient, the information comprising details of individual MR scans of the MR exam;
b) providing by the input unit the information on the MR exam to a processing unit;
c) receiving by the input unit information on the patient on whom the MR exam is to be performed, wherein the information relates to the tolerance to noise of the patient and/or the ability of the patient to remain quiescent;
d) providing by the input unit the information on the MR patient to the processing unit;
e) determining by the processing unit an overall score value for each MR scan of the individual MR scans, the determining comprising utilizing the information on the patient;
f) determining by the processing unit a sequence of MR scans for the MR exam, the determining comprising utilizing the individual MR scans and the overall score value for each MR scan; and
g) outputting by the output unit the determined sequence of MR scans for the MR exam.

15. A non-transitory computer readable medium configured to store computer readable instructions when executed by a processor is configured to carry out the method of claim 14.

* * * * *